US011987783B2

(12) United States Patent
Bhat et al.

(10) Patent No.: US 11,987,783 B2
(45) Date of Patent: May 21, 2024

(54) SYSTEM AND METHOD FOR WIRELESSLY POWERING A SENSOR IN A BIO-PROCESSING ENVIRONMENT

(71) Applicant: Cytiva Sweden AB, Uppsala (SE)

(72) Inventors: Suma Memana Narayana Bhat, Bangalore (IN); Veena B N Rao, Bangalore (IN); Andreas Axen, Uppsala (SE); Deepak Aravind, Bangalore (IN); Nagapriya Kavoori Sethumadhavan, Bangalore (IN); Hanish Lakhani, Bangalore (IN); Purbasha Halder, Bangalore (IN); Victor Jose, Bangalore (IN)

(73) Assignee: Cytiva Sweden AB, Uppsala (SE)

( * ) Notice: Subject to any disclaimer, the term of this patent is extended or adjusted under 35 U.S.C. 154(b) by 496 days.

(21) Appl. No.: 16/607,544

(22) PCT Filed: Apr. 18, 2018

(86) PCT No.: PCT/EP2018/059811
§ 371 (c)(1),
(2) Date: Oct. 23, 2019

(87) PCT Pub. No.: WO2018/197275
PCT Pub. Date: Nov. 1, 2018

(65) Prior Publication Data
US 2020/0071656 A1 Mar. 5, 2020

(30) Foreign Application Priority Data
Apr. 28, 2017 (IN) .............................. 201741015123

(51) Int. Cl.
*H02J 50/00* (2016.01)
*C12M 1/00* (2006.01)
(Continued)

(52) U.S. Cl.
CPC ............ *C12M 27/16* (2013.01); *C12M 21/02* (2013.01); *C12M 43/08* (2013.01); *C12M 47/02* (2013.01);
(Continued)

(58) Field of Classification Search
CPC .......... H02J 50/001; H02J 50/10; H02J 50/12; H02J 50/80; C12M 41/00; C12M 21/00; C12M 27/00; C12M 43/00; C12M 47/00
See application file for complete search history.

(56) References Cited

U.S. PATENT DOCUMENTS

2004/0085562 A1   5/2004  Fromherz
2005/0254055 A1  11/2005  Peng
(Continued)

FOREIGN PATENT DOCUMENTS

CN     102656282     9/2012
CN     101331503    12/2012
(Continued)

OTHER PUBLICATIONS

European Office Action for EP Application No. 18718446.0 dated Nov. 30, 2020 (7 pages).
(Continued)

*Primary Examiner* — Rexford N Barnie
*Assistant Examiner* — Joseph N Inge
(74) *Attorney, Agent, or Firm* — Eversheds Sutherland (US) LLP

(57) ABSTRACT

A bio-processing system (100) for wirelessly powering one or more sensors (116-128, 400) is presented. The system (100) includes bio-processing units (106-110), process supporting devices (112-114), energy sources (146-148), and sensors (116-128, 400) including an energy harvesting unit (402) and an energy storage unit (404). The system (100) includes a power management subsystem (104, 200) wire-
(Continued)

lessly coupled to the sensors (116-128, 400) and including a processor (202) configured to wirelessly monitor energy consumption of the sensors (116-128, 400) and a level of energy stored in corresponding energy storage units (404), select at least one sensor (116-128, 400) based on the energy consumption of the sensors (116-128, 400) and corresponding levels of energy stored in the energy storage units (404), and identify at least one active energy source (146-148) as a power source, where the identified power source is configured to wirelessly transfer power to the selected sensor (116-128, 400).

25 Claims, 6 Drawing Sheets

(51) Int. Cl.
  *C12M 3/06* (2006.01)
  *H02J 7/00* (2006.01)
  *H02J 50/80* (2016.01)
(52) U.S. Cl.
  CPC ........ *H02J 7/00034* (2020.01); *H02J 50/001* (2020.01); *H02J 50/80* (2016.02)

(56) References Cited

U.S. PATENT DOCUMENTS

| | | | |
|---|---|---|---|
| 2007/0243626 A1 | 10/2007 | Windeyer et al. | |
| 2008/0069739 A1 | 3/2008 | Ludwig | |
| 2009/0176301 A1 | 7/2009 | Oldenburg et al. | |
| 2010/0144022 A1* | 6/2010 | Surapaneni | C12M 23/48 435/289.1 |
| 2012/0187897 A1* | 7/2012 | Lenk | H02J 7/00308 320/101 |
| 2012/0256492 A1* | 10/2012 | Song | H02J 50/27 307/64 |
| 2013/0193774 A1 | 8/2013 | Yang et al. | |
| 2014/0175876 A1* | 6/2014 | Cheatham, III | H02J 50/80 307/23 |
| 2014/0212954 A1 | 7/2014 | Auner et al. | |
| 2014/0255910 A1 | 9/2014 | Arnold et al. | |
| 2014/0287449 A1 | 9/2014 | Bonyuet | |
| 2015/0128733 A1* | 5/2015 | Taylor | H02J 50/80 73/865.8 |
| 2015/0137992 A1* | 5/2015 | Potyrailo | G01N 27/3272 340/870.07 |
| 2017/0039441 A1 | 2/2017 | Lim et al. | |

FOREIGN PATENT DOCUMENTS

| | | |
|---|---|---|
| CN | 102859527 | 1/2013 |
| CN | 105471123 | 4/2016 |
| CN | 104769766 | 4/2018 |
| EP | 2774979 A1 | 9/2014 |
| EP | 2822144 A1 | 1/2015 |
| JP | 2015123300 | 7/2015 |
| WO | 2013096842 A2 | 6/2013 |
| WO | 2016/037100 A1 | 3/2016 |

OTHER PUBLICATIONS

European Office Action for EP Application No. 18718447.8 dated Dec. 2, 2020 (7 pages).
PCT International Search Report and Written Opinion for PCT Application No. PCT/EP2018/059811 dated Jul. 26, 2018 (9 pages).
"BioProcess Product Guide 2012/2013", GE Healthcare Life Sciences, 2014, pp. 1-20.
"Integrated Bioprocess Solutions", Millipore Sigma, 2016, pp. 1-24.
International Search Report for PCT Application No. 2018/059810 dated Jul. 19, 2018 (9 pages).
International Search Report for PCT Application No. 2018/059809 dated Aug. 21, 2018 (10 pages).
Wikipedia contributors. (Aug. 25, 2022). Wireless. In Wikipedia, The Free Encyclopedia. Retrieved 17:11, Aug. 30, 2022, from https://en.wikipedia.org/w/index.php?title=Wireless&oldid=1106637765lf.
China National Intellectual Property Administration (CNIPA), First Office Action & Search Report for CN Application No. 20188027625.3 dated Feb. 2, 2023, (35 pages, including Reporting Letter and English translations).
U.S. Non Final Office Action for corresponding U.S. Appl. No. 16/605,115, mailed Apr. 28, 2023, 23 pages.
China National Intellectual Property Administration (CNIPA), First Office Action & Search Report for CN Application No. 201880027789.6 dated Jan. 20, 2023, (36 pages including English translations).

* cited by examiner

SYSTEM AND METHOD FOR WIRELESSLY POWERING A SENSOR IN A BIO-PROCESSING ENVIRONMENT

CROSS REFERENCE TO RELATED APPLICATIONS

This application claims the priority benefit of PCT/EP2018/059811 filed on Apr. 18, 2018, which claims priority benefit of India Patent Application No. 201741015123 filed on Apr. 28, 2017, the entire contents of which are hereby incorporated by reference herein.

TECHNICAL FIELD

Embodiments of the present specification relate generally to a bio-processing system/environment, and more specifically to a system and method for wirelessly powering a sensor in the bio-processing environment.

BACKGROUND

As will be appreciated, bio-processing systems are employed to perform various bio-processing operations. Some examples of these bio-processing operations include processing of genetically engineered organisms, cells, constituents of cells such as bacteria, enzymes, chloroplasts to obtain desired products such as vaccines, hormones, plasma proteins, monoclonal antibodies, pharmaceuticals, and the like. Currently available bio-processing systems entail use of several units such as bioreactors, harvesting units, chromatography units, filtration units, buffer preparation units, buffer holding units, media holding units, pumps, temperature management devices, flow control clamps, sensors, and the like, to perform the bio-processing operations.

Traditionally, the units in the bio-processing systems are mechanically and/or electrically coupled to one another to facilitate the bio-processing operations. By way of example, the units in the bio-processing system may be mechanically hardwired to one another via steel pipes to provide passage for transfer of fluids between the units. In addition, these units in the bio-processing system are powered and controlled via a wired electrical network. Modifying the hardwired configuration of the currently available bio-processing systems is a challenging and laborious task. Additionally, the wired electrical connections in the currently available bio-processing systems impede easy monitoring and controlling of the various operations in the bio-processing systems. By way of example, placement of sensors in the bio-processing systems is hampered by the need for numerous wired connections. Moreover, powering these sensors is also a time-consuming and arduous task.

Moreover, single-use units for use in bio-processing applications is gaining popularity as these units provides a lower cost solution in comparison to the traditionally used units that entail use of stainless steel products. By way of example, use of flexible, disposable units such as cell bags and pipes offer advantages such as improved sterility, cleanability, reduced cycle time, and the like.

SUMMARY

In accordance with certain aspects of the present specification, a bio-processing system for wirelessly powering one or more sensors is presented. The system includes one or more bio-processing units configured to perform at least one bio-processing operation. Moreover, the system includes one or more process supporting devices operatively coupled to the one or more bio-processing units, where the one or more process supporting devices are configured to aid the one or more bio-processing units in performing the at least one bio-processing operation. In addition, the system includes one or more energy sources, where the one or more energy sources include one or more active energy sources and one or more ambient energy sources. The system also includes one or more sensors operatively coupled to at least one of the one or more bio-processing units and the one or more process supporting devices, where at least one sensor of the one or more sensors includes an energy harvesting unit configured to harvest energy from at least one energy source of the one or more energy sources, and an energy storage unit operatively coupled to the energy harvesting unit and configured to store the harvested energy. Furthermore the system includes a power management subsystem wirelessly coupled to the one or more sensors, where the power management subsystem includes a processor configured to wirelessly monitor energy consumption of the one or more sensors and a level of energy stored in corresponding energy storage units of the one or more sensors, select at least one sensor of the one or more sensors based on the energy consumption of the one or more sensors and corresponding levels of energy stored in the energy storage units of the one or more sensors, and identify at least one active energy source of the one or more active energy sources as a power source, where the identified power source is configured to wirelessly transfer power to the selected at least one sensor.

In accordance with another aspect of the present specification, a method for wirelessly powering one or more sensors in a bio-processing system including one or more bio-processing units, one or more process supporting devices, the one or more sensors, one or more energy sources, and a power management subsystem is presented. The method includes wirelessly harvesting, via an energy harvesting unit in the one or more sensors, energy from at least one energy source of the one or more energy sources in the bio-processing system, where the one more energy sources includes one or more active energy sources and one or more ambient energy sources. Further, the method includes storing, via an energy storage unit in the one or more sensors, the harvested energy. In addition, the method includes wirelessly monitoring, via a processor in the power management subsystem, energy consumption of the one or more sensors and a level of energy stored in corresponding energy storage units of the one or more sensors. Moreover, the method includes selecting at least one sensor of the one or more sensors based on the energy consumption of the one or more sensors and corresponding levels of energy stored in the energy storage units of the one or more sensors. Also, the method includes identifying at least one active energy source of the one or more energy sources as a power source, where the identified power source is configured to wirelessly power to the selected at least one sensor.

In accordance with yet another aspect of the present specification, a power management subsystem for wirelessly powering one or more sensors in a bio-processing system, the bio-processing system including one or more bio-processing units, one or more process supporting devices operatively coupled to the one or more bio-processing units, one or more energy sources including one or more active energy sources and one or more ambient energy sources, the one or more sensors operatively coupled to at least one of the one or more bio-processing units and the one or more process supporting devices, where the power management subsystem is wirelessly coupled to the one or more sensors is presented. The power management subsystem includes a processor configured to wirelessly monitor energy consumption of the one or more sensors and a level of energy stored in corresponding energy storage units of the one or more sensors, select at least one sensor of the one or more sensors based on the energy consumption of the one or more sensors and corresponding levels of energy stored in the energy storage units of the one or more sensors, and identify at least one active energy source of the one or more active energy sources as a power source, where the identified power source is configured to wirelessly transfer power to the selected at least one sensor.

DRAWINGS

These and other features and aspects of embodiments of the present specification will become better understood when the following detailed description is read with references to the accompanying drawings in which like characters represent like parts throughout the drawings, wherein.

DETAILED DESCRIPTION

As will be described in detail hereinafter, various embodiments of an exemplary system and method for wirelessly powering a sensor in a bio-processing system are presented. Use of these systems and methods greatly reduces the need for wired connections between all the sensors in the bio-processing system, thereby enhancing the workflow and reducing the cost of the bio-processing system and wear and tear of any wires/connectors. Additionally, the system and methods presented hereinafter allow a self-powering, self-sustained operation of the sensors in the bio-processing system.

In the effort to provide a concise description of these embodiments, all features of an actual implementation may not be described in the specification. It should be appreciated that in the development of any such actual implementation, as in any engineering or design project, numerous implementation-specific decisions must be made to achieve the developer's specific goals such as compliance with system-related and business-related constraints.

When describing elements of the various embodiments of the present specification, the articles "a", "an", "the" and "said" are intended to mean that there are one or more of the elements. The terms "comprising", "including" and "having" are intended to be inclusive and mean that there may be additional elements other than the listed elements. Furthermore, the terms "build" and "construct" and their variations are intended to mean a mathematical determination or computation of mathematical constructs. The terms "data drawn on arbitrary domains" or "data on arbitrary domains" are intended to mean data corresponding to a domain for example, social media data, sensor data, enterprise data and the like.

Figure 1:
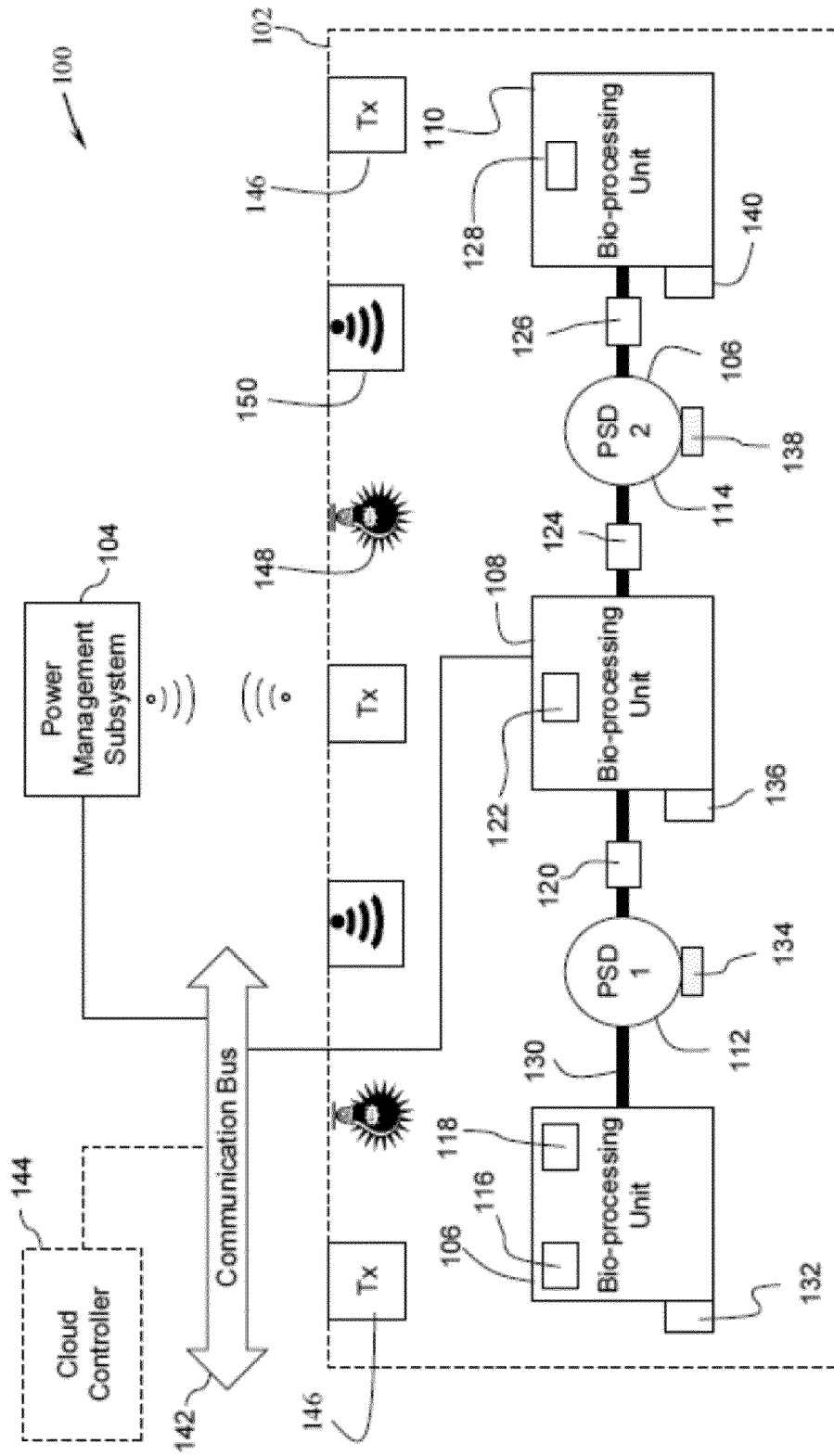
FIG. 1 is a schematic diagram of a bio-processing system including a power management subsystem configured to wirelessly power a sensor in the bio-processing system, in accordance with aspects of the present specification.

FIG. 1 is a diagrammatic representation of a bio-processing system (100), in accordance with aspects of the present specification. In a presently contemplated configuration, the bio-processing system (100) includes one or more bio-processing units (106, 108, 110), one or more process supporting devices (112, 114), one or more sensors (116, 118, 120, 122, 124, 126), one or more energy sources (146, 148, 150), or combinations thereof. The energy sources include one or more active energy sources (146, 148) and one or more ambient energy sources (150). Additionally, the bio-processing system (100) includes a power management subsystem (104) configured to manage/control supply of power to the various components of the bio-processing system (100). The bio-processing system (100) may be operated to perform various bio-processing operations that entail processing of genetically engineered organisms, cells, constituents of cells such as bacteria, enzymes, chloroplasts to obtain desired products such as vaccines, hormones, plasma proteins, monoclonal antibodies, or pharmaceuticals, or combinations thereof.

As depicted in the embodiment of FIG. 1, the bio-processing system (100) includes the bio-processing units (106, 108, 110). The bio-processing system (100) further includes the process supporting devices (112, 114). In addition, the bio-processing system (100) includes the sensors (116, 118, 120, 122, 124, 126, 128). The bio-processing units (106, 108, 110) may be collectively referred to as the bio-processing units (106-110). Also, the process supporting devices (112, 114) may be collectively referred to as the process supporting devices (112-114). In a similar fashion, the sensors (116, 118, 120, 122, 124, 126, 128) may collectively referred to as the sensors (116-128). Moreover, the active energy sources (146, 148) and the ambient energy source (150) (for example, an ambient radio-frequency (RF) source) may be collectively referred to as the energy sources (146-150). Furthermore, the collection of the bio-processing units (106-110), the process supporting devices (112-114), and the sensors (116-128) may generally be referred to as a bio-processing environment (102).

In some embodiments, the bio-processing environment (102) may also include one or more disposable fluid coupling tubes (130) and one or more smart switching devices (132, 134, 136, 138, 140). The smart switching devices (132, 134, 136, 138, 140) may be collectively referred to as the smart switching devices (132-140). In one example, the disposable fluid coupling tubes (130) are made using polymeric materials and are used to provide fluid coupling between one or more of the bio-processing units (106-110), the process supporting devices (112-114), and the sensors (116-128). In some embodiments, the disposable fluid coupling tubes (130) may be capable of being warped in any direction to establish a flexible fluid coupling. Some examples of the polymeric material include, but are not limited to, silicone, PVC, polyurethane, fluoropolymers, thermoplastic elastomers, polycarbonate, polysulfone, polyethylene, or combinations thereof.

In certain embodiments, the bio-processing system (100) may also a communication bus (142) configured to facilitate communicatively coupling the various bio-processing units (106-110), process supporting devices (112-114), and sensors (116-128) in the bio-processing environment 102. The communication bus (142) may be a field bus such as Probus®, Modbus®, Controller Area Network (CAN) bus, FOUNDATION Fieldbus® or an industrial Ethernet bus such Transmission Control Protocol/Internet Protocol (TCP/IP) bus, Modbus® TCP bus, Profinet® Ethernet bus, EtherCAT® Ethernet bus, or combinations thereof. Moreover, the bio-processing system (100) may include a cloud controller (144). Further, in some embodiments, the power management subsystem (104) may be implemented on an Internet cloud as the cloud controller (144).

The bio-processing units (106-110) may be configured to perform at least one bio-processing operation. Non-limiting examples of the bio-processing units (106-110) include a bioreactor for cell cultivation, a flexible bag bioreactor, a cell banking unit, a cell harvesting unit, a chromatography unit, a wave rocker, a protein concentration unit, a sterile filtration unit, a virus removal unit, a product holding unit, a buffer preparation unit, a media preparation unit, a buffer holding unit, a media holding unit, or combinations thereof. It may be noted that although the embodiment of the bio-processing system (100) of FIG. 1 depicts use of three bio-processing units (106-110), use of greater than three or lower than three bio-processing units is also envisioned. In some embodiments, the flexible cell bag may be formed using polymeric materials, thereby enabling a single, disposable use of the flexible cell bag. Some examples of the polymeric material include, but are not limited to, silicone, PVC, polyurethane, fluoropolymers, thermoplastic elastomers, polycarbonate, polysulfone, polyethylene, or combinations thereof.

Also, in the bio-processing environment (102), the bio-processing units (106-110) may be arranged to perform upstream sub-processes or downstream sub-processes of the bio-processing operation. By way of example, one or more of the bio-processing units (106-110) may be configured to perform the upstream sub-processes, while the remaining bio-processing units (106-110) may be configured to perform the downstream sub-processes. Some non-limiting examples of the upstream sub-processes include a cell bank preparation, seed culture expansion, seed production, seed harvesting, or combinations thereof. Similarly, some non-limiting examples of the downstream sub-processes may include chromatography, separation, cell disruption, broth concentration, purification, de-watering, polishing of metabolites, filtration, formulation of a final product, or combinations thereof.

Further, the process supporting devices (112-114) are operatively coupled to one or more of the bio-processing units (106-110) and configured aid the bio-processing units (106-110) in performing the bio-processing operation. Some non-limiting examples of the process supporting devices (112-114) include a pump, a weighing scale, a flow restriction clamp, a temperature management device, or combinations thereof. In one example, the process supporting device (112) in the form of a flow restriction clamp may be disposed along a disposable fluid coupling tube (130) between the two bio-processing units (106) and (108) to aid in restricting a flow rate of a fluid from the bio-processing unit (106) to the bio-processing unit (108). In another example, the process supporting device (114) in the form of a pump may be disposed along a disposable fluid coupling tube (130) between the two bio-processing units (108) and (110) to aid in transferring a fluid from the bio-processing unit (108) to the bio-processing unit (110). In yet another example, a process supporting device such as a temperature management device may be used to maintain a temperature of the fluid within the bio-processing units (106-110) or within the disposable fluid coupling tube (130) at a determined level.

As noted hereinabove, the bio-processing system (100) may also include one or more active energy sources (146-148) and one or more ambient energy sources (150) in or around the bio-processing environment (102). By way of example, the active energy sources may include an RF source such as a RF transmitter (146), a light source (148), a heat source, a vibration source, an ultrasound energy source, or combinations thereof. Also, the ambient energy sources may include an ambient temperature, an ambient pressure, an ambient light, an ambient RF source (150), or combinations thereof. The ambient RF source (150) may be a Wi-Fi router, for example.

Moreover, the sensors (116-128) are operatively coupled to at least one of the bio-processing units (106-110) and the process supporting devices (112-114) and configured to monitor one or more process parameters. The process parameters are generally representative of parameters associated with the bio-processing operation being performed by the bio-processing system (100). Some non-limiting examples of the process parameters are, pH, glucose, glutamine, lactate, glutamate, ammonia, cell viability/non-viability, and the like. In one embodiment, one or more sensors (116-128) may be disposed within the bio-processing units (106-110). By way of example, if the bio-processing unit is a flexible bag bioreactor, the sensors (116-128) may be embedded in a flexible cell bag of the bioreactor. It may be noted that the flexible cell bag in the bioreactor may be a single-use, disposable cell bag. Additionally or alternatively, one or more sensors (116-128) may be disposed along or within the disposable fluid coupling tubes (130) between the bio-processing units (106-110). In the example of FIG. 1, sensors (116, 118, 122 and 128) are disposed within the bio-processing units (106-110), while the sensors (120, 124, are 126) are disposed along the disposable fluid coupling tubes (130) between the bio-processing units (106-110).

Also, some non-limiting examples of the sensors (116-128) include a pressure sensor, a temperature sensor, a pH sensor, a conductivity sensor, a glucose sensor, a biomass sensor, a cell viability sensor, an oxygen sensor, a carbon-dioxide sensor, an ultraviolet (UV) sensor, a flow sensor, a foam sensor, or combinations thereof. In addition, some examples of the process parameters monitored by these sensors (116-128) may include a pressure of the fluid in the disposable fluid coupling tubes (130), a temperature of the fluid, a pH of the fluid, presence of a biomass in the fluid, an electrical conductivity of the fluid, a level of glucose in the fluid, a cell viability in the fluid, a level of oxygen in the bio-processing units (106-110), a level of carbon-dioxide in the bio-processing units (106-110), a flow rate of the fluid, a level of foam in the fluid in the bio-processing units (106-110), or combinations thereof.

Figure 4:
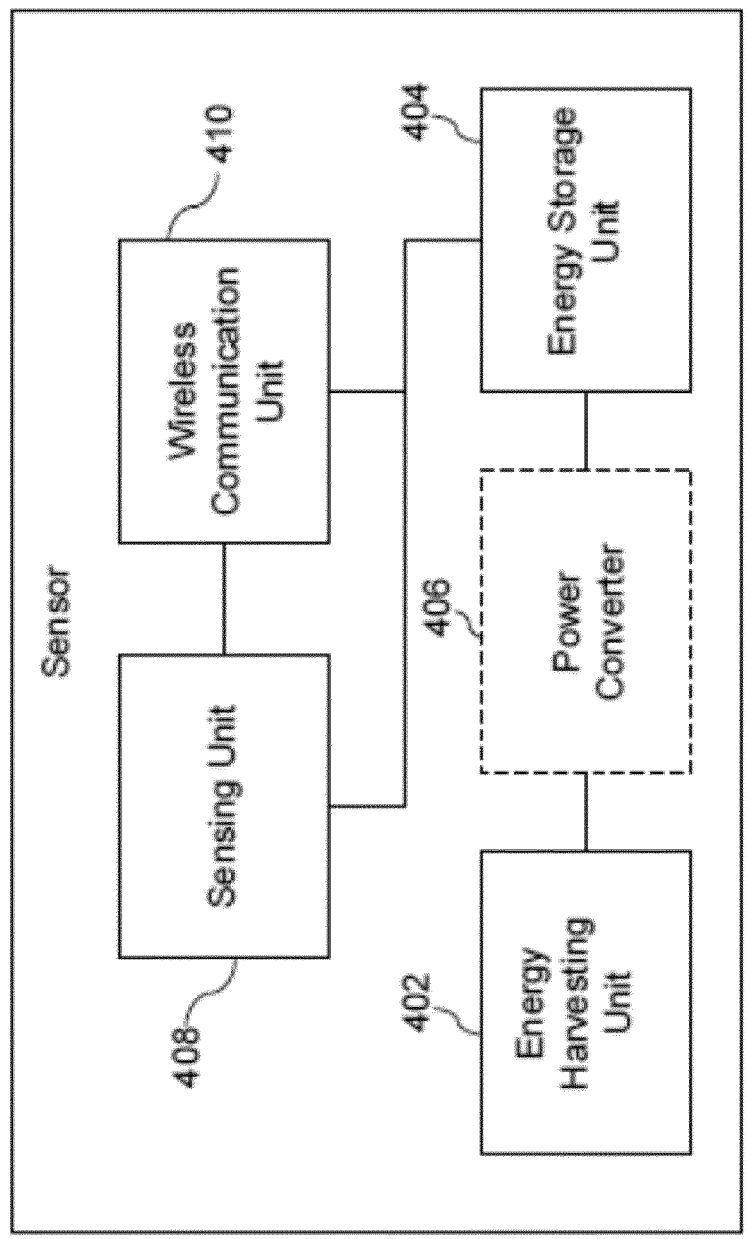
FIG. 4 is a diagrammatic representation of a sensor for use in the bio-processing system of FIG. 1, in accordance with aspects of the present specification.

In accordance with aspects of the present specification, one or more of the sensors (116-128) include an energy harvesting unit, an energy storage unit, a sensing unit, and a wireless communication unit (see FIG. 4). Additionally, the sensor may include a power converter. Furthermore, these sensors (116-128) are configured to be self-powering sensors. To that end, the sensors are configured to harvest energy from one or more of the active energy sources and/or one or more of the ambient energy sources in the bio-processing environment (102). The harvested energy is then stored in the energy storage unit of the sensors (116-128). In certain embodiments, the power converter may be used to boost a level of the harvested energy. Various components of the sensors (116-128) are powered using the stored energy. The working of the sensors (116-128) will be described in greater detail with reference to FIG. 4.

In some embodiments, one or more of the bio-processing units (106-110), the process supporting devices (112-114), and the sensors (116-128) may include a wireless communication unit (not shown). The wireless communication unit may be configured to establish a wireless connection between one or more of the bio-processing units (106-110), the process supporting devices (112-114), and the sensors (116-128) and the power management subsystem (104) and/or the cloud controller (144). In certain embodiments, the wireless communication unit may be implemented using hardware and/or software. The wireless communication unit may also include circuits capable of communicating with the power management subsystem (104) and/or the cloud controller (144) via wireless communication techniques such as, but not limited to, infrared, short-range radio frequency (RF) communication, Bluetooth, Bluetooth low energy (BLE), Wi-Fi, Wi-Max, mobile communication techniques such as Global System for Mobile communication (GSM), General Packet Radio Service (GPRS), Code Division Multiple Access (CDMA), High-Speed Downlink Packet Access (HSDPA), 2.5G, 3G, 4G, 5G, or combinations thereof.

Further, in certain embodiments, the bio-processing environment (102) may also include the one or more smart switching devices (132-140). In the presently contemplated configuration of FIG. 1, one smart switching device is shown as being coupled to each of the bio-processing units (106-110) and the process supporting devices (112-114). It may be noted that the bio-processing units (106-110) and the process supporting devices (112-114) are configured to receive electrical power from an electrical port (not shown) via a corresponding smart switching device. In the example of FIG. 1, the bio-processing units (106, 108, and 110) are coupled to their respective electrical power ports via corresponding smart switching devices (132, 136, and 140). Similarly, the process supporting devices (112, 114) are coupled to their respective electrical power ports via corresponding smart switching devices (134 and 138).

Moreover, in one embodiment, each smart switching device (132-140) may include an input port, an output port, a wireless communication unit, and a switch controllable via the wireless communication unit. The wireless communication of the smart switching device (132-140) may be similar to the wireless communication unit of the bio-processing units (106-110), the process supporting devices (112-114), and the sensors (116-128). The input port of the smart switching device (132-140) is coupled to an electrical power port to receive electrical power. The output port of the smart switching device (132-140) is coupled to a corresponding bio-processing unit (106-110) or process supporting device (112-114) to supply the electrical power depending on an operating state of the switch. It may be noted that the switch may be controlled to enable or disable an electrical connection between the input port and the output port of the smart switching device (132-140), thereby controlling the supply of power to the bio-processing units (106-110) and/or the process supporting devices (112-114).

As previously noted, the bio-processing system (100) includes the exemplary power management subsystem (104). The power management subsystem (104) is wirelessly coupled to at least one of the one or more bio-processing units (106-110), the one or more process supporting devices (112-114), and the one or more sensors (116-128). In some embodiments, the power management subsystem (104) may be coupled to one or more of the bio-processing units (106-110) via the communication bus (142).

Although the embodiment of FIG. 1 depicts the power management subsystem (104) as being disposed external to the bio-processing environment (102), in some embodiments, the power management subsystem (104) may be disposed locally within the bio-processing environment (102). In certain other embodiments, the power management subsystem (104) may be disposed at a location remote from the bio-processing environment (102).

The power management subsystem (104) may be configured to wirelessly power one or more sensors (116-128). In one embodiment, the power management subsystem (104) includes a processor, a display unit, a memory unit, and a master wireless communication unit (see FIG. 2) that are configured to aid in wirelessly powering at least one sensor of the one or more sensors (116-128) in the bio-processing environment (102). In certain embodiments, the processor of the power management subsystem (104) is configured to wirelessly monitor energy consumption of the sensors (116-128) and a level of energy stored in corresponding energy storage units of the sensors (116-128). The energy consumption may be representative of a rate of energy consumption by the sensor (400). The rate of energy consumption may be represented as mW/hour or Watts/hour.

Furthermore, the processor is configured to select/identify a sensor from the one or more sensors (116-128) based on the energy consumption of the sensors (116-128) and corresponding levels of energy stored in the energy storage units of the sensors (116-128). More particularly, the processor is configured to identify one or more sensors that are energy deficient. These energy deficient sensors are representative of those sensors that are unable to power themselves and enable a self-sustaining sensor operation. If such an energy deficient sensor is identified, the processor (202) is configured to identify at least one active energy source of the active energy sources (146-148) as a power source for powering the energy deficient sensors. In particular, the identified active power source is configured to wirelessly transfer power to the selected energy deficient sensor to fulfill the energy deficit or shortfall of that sensor. By way of example, if the sensor (116) is identified as an energy deficient sensor, the processor may identify the RF source (146) as the power source. The RF source (146) may be configured to wirelessly transfer power to the energy harvesting unit of the sensor (116), thereby fulfilling the energy deficiency of the sensor (116).

In accordance with further aspects of the present specification, the power management subsystem (104) may also be configured to generate a power management user interface (see FIG. 3) based on the sensors (116-128), the active energy sources (146-148), the ambient energy sources (150), the energy consumption of a given sensor such as an energy deficient sensor, the level of energy stored in the energy storage unit of that sensor, or combinations thereof. The power management user interface provides one or more recommendations for powering the energy deficient sensor. In addition, the processor is configured to visualize the power management user interface on the display unit of the power management subsystem (104).

Moreover, in certain embodiments, the power management user interface allows a user to manually select a type of sensor, the power source, and the like. Further, the power management subsystem (104) is configured to receive the user selection as control inputs from the power management user interface. The power management subsystem (104) is further configured to activate the identified power source to wirelessly transfer power to the selected energy deficient sensor. The working of the power management subsystem (104) will be described in greater detail with reference to FIG. 2.

Figure 2:
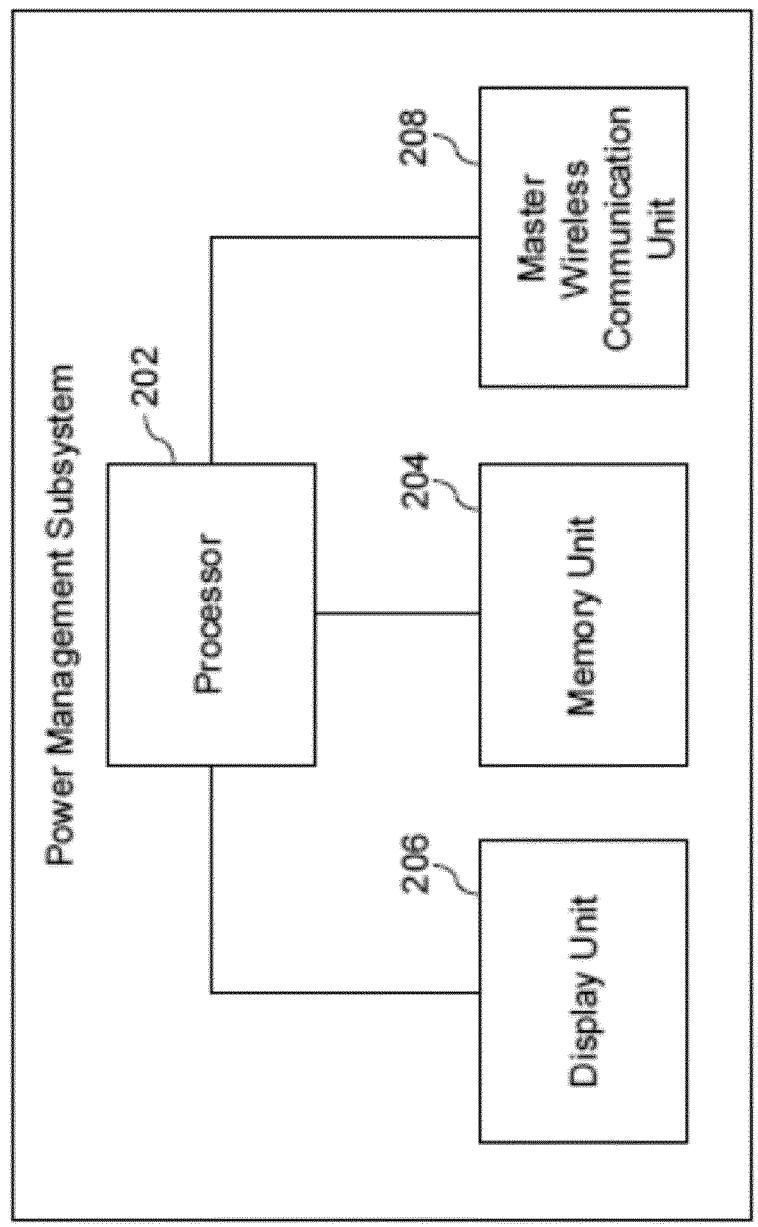
FIG. 2 is a diagrammatic representation a power management subsystem for use in the bio-processing system of FIG. 1, in accordance with aspects of the present specification.

Referring now to FIG. 2, a diagrammatic representation of a power management subsystem, in accordance with aspects of the present specification, is presented. The power management subsystem (200) is representative of one embodiment of the power management subsystem (104) of FIG. 1. FIG. 2 is described with reference to the components of FIG. 1. As previously noted, the power management subsystem 200 is configured to manage/control supply of power to the various components of the bio-processing system 100.

In a presently contemplated configuration, the power management subsystem (104) includes a processor (202), a memory unit (204), a display unit (206), and a master wireless communication unit (208). The processor (202) is coupled to one or more of the memory unit (204), the display unit (206), and the master wireless communication unit (208) and configured to control operations of the power management subsystem (200).

In one embodiment, the processor (202) may include hardware such as electronic circuits, software, and/or firmware for performing various arithmetic, logical, and graphics processing operations. The processor (202) may be an integrated circuit (IC) chip. Also, the processor (202) may have one or more processing cores to aid in the arithmetic, logical, and graphics processing operations.

As previously noted with reference to FIG. 1, the processor (202) is configured to wirelessly monitor the energy consumption of sensors (116-128) and a level of energy stored in corresponding energy storage units (404) of the sensors (116-128). Moreover, the processor (202) is configured to select/identify at least one sensor of the sensors (116-128) as an energy deficient sensor based on the energy consumption of the sensors (116-128) and the corresponding levels of energy stored in the energy storage units (404) of these (116-128). To that end, the processor (202) is configured to generate a power management user interface. In particular, the processor (202) is configured to create one or more recommendations for powering the energy deficient sensor.

Moreover, the processor (202) is also configured to identify at least one active energy source of the one or more active energy sources (146-148) as a power source, where the identified power source is configured to wirelessly transfer power to the energy deficient sensor. The processor (202) may be further configured to visualize the power management user interface (300) on the display unit (206) to allow a user to provide control inputs. Additionally, the processor (202) is configured to activate the identified power source based on the control inputs to power the energy deficient sensor.

Further, the memory unit (204) may be configured to store data and program instructions for use by the processor (202). By way of example, the memory unit (204) may include random access memory (RAM) such as a static RAM (SRAM) and a dynamic RAM (DRAM), a read-only memory (ROM) such as a masked ROM (MROM), a programmable read only memory (PROM), an erasable and programmable read only memory (EPROM), and an electrically erasable and programmable read only memory (EEPROM). Moreover, the memory unit (204) may be in the form of a compact disc (CD), a digital versatile disc (DVD), a floppy disc, a USB flash drive, a cloud based memory, or combinations thereof.

In some embodiments, the memory unit (204) may be configured to store a data repository. The data repository may include a catalog and/or a look-up table of the bio-processing units (106-110), the process supporting devices (112-114), the sensors (116-128), the smart switching devices (132-140), the active energy sources (146-148), the ambient energy sources (150), one or more workflow types, or combinations thereof. In particular, the catalog and/or look-up table may include identity information, such as a unique ID corresponding to the bio-processing units (106-110), the process supporting devices (112-114), the sensors (116-128), the smart switching devices (132-140), one or more process steps, one or more types of bio-processing workflows, desired power requirements of the sensors (116-128), and the like. The unique ID may include a name, a numerical value, a special character, a symbol, or combinations thereof. The catalog and/or the look-up table may be updated to include identity information corresponding to any new bio-processing units, process supporting devices, sensors, process steps, disposable fluid coupling tubes that are introduced into the bio-processing environment (102).

Moreover, the display unit (206) may be implemented using a cathode ray tube (CRT) display, a liquid crystal display (LCD), a light-emitting diode (LED) display, a plasma display, a projector, or combinations thereof. In some embodiments, the display unit (206) may be a touch-screen based display. The display unit (206) may be configured to receive commands and/or data from the processor (202) and update the displayed information based on the received commands and/or data. More particularly, a user interface such as a power management user interface (see FIG. 3) may be visualized on the display unit (206) by the processor (202).

In addition, the master wireless communication unit (208) may be implemented using hardware and/or software. The master wireless communication unit (208) may also include circuits capable of wirelessly communicating with wireless communication units of the bio-processing units (106-110), the process supporting devices (112-114), the sensors (116-128), and the smart switching devices (132-140). The master wireless communication unit (208) is wirelessly coupled to the wireless communication units corresponding to the bio-processing units (106-110), the process supporting devices (112-114), the sensors (116-128), and the smart switching devices (132-140).

Moreover, the master wireless communication unit (208) is configured to facilitate communication of control commands and/or data between the processor (202) and the bio-processing units (106-110), the process supporting devices (112-114), the sensors (116-128), and the smart switching devices (132-140). In particular, the master wireless communication unit (208) may be configured to communicate the control commands and/or the data via wireless communication techniques such as, but not limited to, infrared, short-range radio frequency (RF) communication, Bluetooth, Bluetooth low energy (BLE), Wi-Fi, Wi-Max, mobile communication techniques such as Global System for Mobile communication (GSM), General Packet Radio Service (GPRS), Code Division Multiple Access (CDMA), High-Speed Downlink Packet Access (HSDPA), 2.5G, 3G, 4G, 5G, or combinations thereof.

Figure 3:
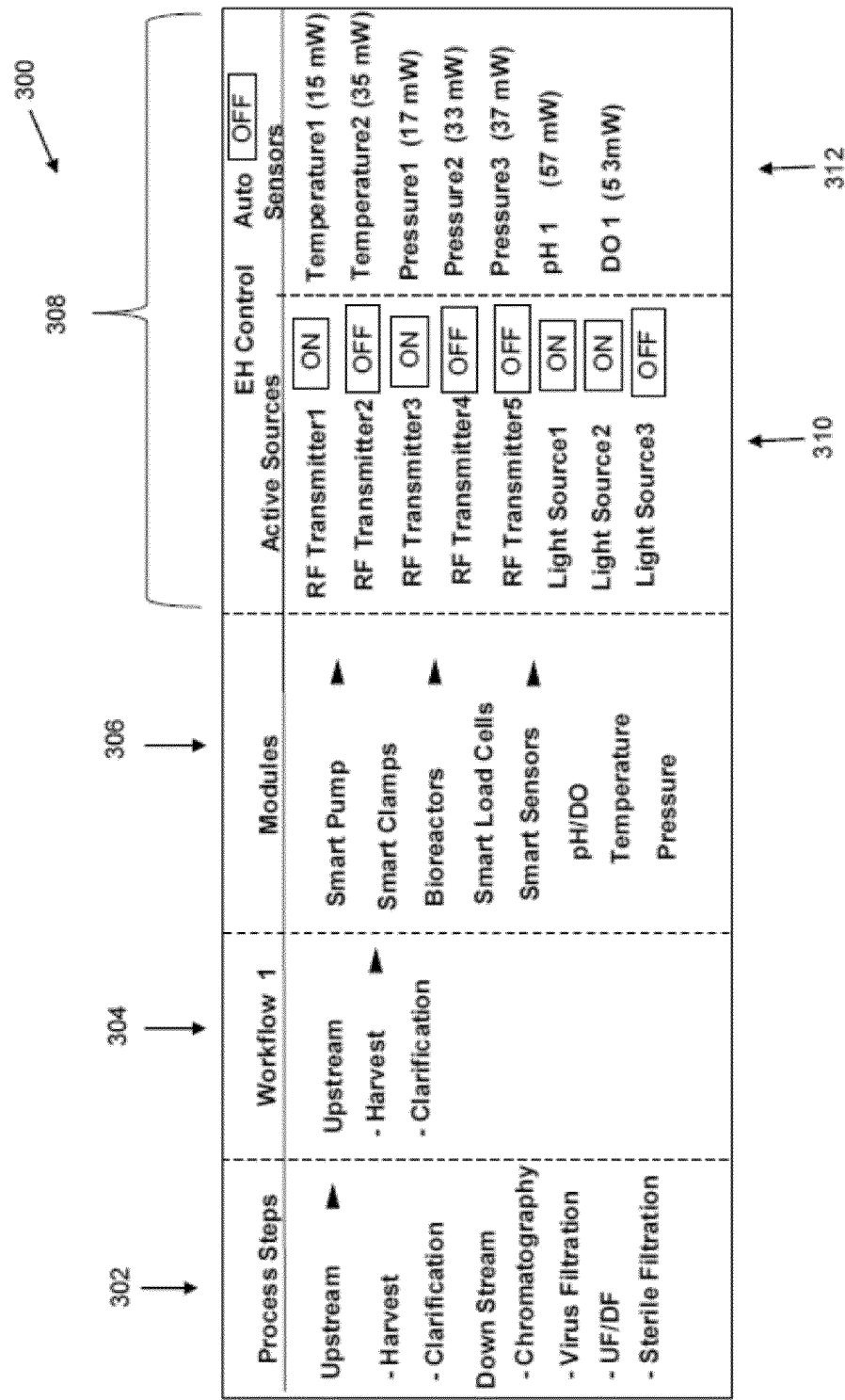
FIG. 3 is a diagrammatic representation of an exemplary power management user interface generated by the power management subsystem of FIG. 2, in accordance with aspects of the present specification.

FIG. 3 is a diagrammatic representation of one example of a power management user interface (300) generated by the power management subsystem (200) of FIG. 2, in accordance with aspects of the present specification. Also, FIG. 3 is described with reference to the components of FIGS. 1-2. The power management user interface (300) is generated by the processor (202) of the power management subsystem (200) using a catalog/look-up table stored in a data repository of the memory unit (204). As previously noted, the processor (202) is configured to visualize the power management user interface (300) on the display unit (206).

In the example depicted in FIG. 3, the power management user interface (300) is shown as including one or more columns or vertical portions. A first column (302) represents workflow process steps/types that are performed in the bio-processing environment (102). In a similar fashion, a second column (304) is representative of workflow sub-processes, while a third column (306) is representative a type of component used in the bio-processing environment (102). Moreover, a fourth column (308) represents energy harvest (EH) control options. Although the power management user interface (300) is visualized in a columnar format, use of other types of formats such as dropdown lists, radial buttons, individual icons, or combinations thereof, is also contemplated.

Further, in one example, the power management user interface (300) allows the user to select a workflow process type/step using the options in the first column (302). Based on the selection corresponding to the workflow process type, workflow sub-processes corresponding to the selected workflow process type may be displayed in the second column (304). Once the user makes a selection using the options presented in the second column (304), the third column (306) is populated with types of components corresponding to the selected workflow sub-process and visualized on the power management user interface (300).

The fourth column (308) includes a list of EH control options. In one example, the EH control options (308) include a list of active energy sources (310) and a list of sensors (312). In some embodiments, the EH control (308) may be configured to display information corresponding to the existing workflow by default. Accordingly, in one example, the list of active energy sources (310) includes information related to the active energy sources (310) currently employed in an existing bio-processing workflow in the bio-processing environment (102) and respective operating status such as 'ON" and "OFF" of the active energy sources (310). The operating status "ON" indicates that the corresponding active energy source (310) is activated, while the operating status "OFF" indicates that the corresponding active energy source is deactivated. In certain embodiments, the status indicators "ON" and "OFF" may be in the form of toggle buttons. Such toggle buttons may be activated and deactivated to selectively activate or deactivate the corresponding active energy source (310).

Moreover, in one example, the list of sensors (312) includes information related to the sensors employed in the existing bio-processing workflow. Additionally, a respective strength of received power may also be displayed alongside the corresponding sensor. In one embodiment, the displayed strength of the received power may represent the energy harvested by that sensor. By way of example, a first entry in the list of sensors (312) indicates that the sensor "Temperature1" has 15 mW of harvested energy. Such a visualization of the harvested energy provides an indication regarding an energy deficiency and/or an additional energy requirement, if any, corresponding to that sensor. This visual representation allows the user to make an optimized selection of the power source to power the energy deficient sensors.

Turning now to FIG. 4, a diagrammatic representation of a sensor (400) for use in the bio-processing system (100) of FIG. 1 is presented. It may be noted that the sensor (400) may be representative of one embodiment of the sensors (116-128) of FIG. 1. As previously noted, the sensor (400) is operatively coupled to at least one of the one or more bio-processing units (106-110) and the one or more process supporting devices (112-114). Also, the sensor (400) may include a pressure sensor, a temperature sensor, a pH sensor, a conductivity sensor, a glucose sensor, a biomass sensor, a cell viability sensor, an oxygen sensor, a carbon-dioxide sensor, an ultraviolet (UV) sensor, a flow sensor, a foam sensor, or combinations thereof. FIG. 4 is described with reference to the components of FIGS. 1-3.

In a presently contemplated configuration, the sensor (400) includes an energy harvesting unit (402) and an energy storage unit (404). The energy harvesting unit (402) is configured to wirelessly harvest or extract energy from one or more of the active energy sources (146-148) and the ambient energy sources (150) in the bio-processing environment 102. The active energy sources include the RF source (146), the light source 148, a heat source, a vibration source, or combinations thereof. Also, the ambient energy sources include the ambient RF source (150), an ambient temperature, an ambient pressure, an ambient light, or combinations thereof Further, in one embodiment, the energy harvesting unit (402) includes a thermo-electric generator, a Peltier element, a photovoltaic module, an electromagnetic power generation module, a piezo electric device, an inductive device, or combinations thereof. As will be appreciated, a bio-processing unit such as a bio-reactor in the bio-processing system (100) includes a heater pad on a tray/vessel that is used to maintain the temperature of a medium in a cell bag. In the example where the energy harvesting unit (402) includes a Peltier element/plate, the Peltier element is disposed proximate the heater pad. In certain embodiments, if a hot surface of the Peltier element is disposed in direct contact with the heater pad and a cooler surface of the Peltier element is shielded using a thermal insulator, temperature gradients in excess of 2° C. may be obtained. In this example, the Peltier element is capable of harvesting energy in a range from about 15 mV to about 25 mV even with a temperature gradient of 2° C.

In accordance with aspects of the present specification, the harvested energy is stored in the energy storage unit (404). In some embodiments, the energy storage unit (404) may include a rechargeable battery, a solid-state battery, a capacitor such as a super capacitor or an ultra-capacitor, and the like. The harvested energy so stored in the energy storage unit (404) may be used to power/energize the sensor (400). In other embodiments, the stored energy may also be used to power a wireless communication unit for communication of data.

Furthermore, in certain embodiments, the sensor (400) may also include a power converter (406) disposed between the energy harvesting unit (402) and the energy storage unit (404). The power converter (406) is configured to convert the energy harvested by the energy harvesting unit (402) to enable efficient storage in the energy storage unit (404). Also, the power converter (406) may be configured to boost/enhance a level of the harvested energy prior to storage in the energy storage unit (404).

Moreover, the sensor (400) includes a sensing unit (408) configured to sense at least one process parameter corresponding to the bio-processing operation performed by the bio-processing system (100). Some examples of the sensing unit (408), include sensing elements such as, but not limited to, a pressure sensing element, a piezo electric element, a thermocouple, an integrated circuit temperature sensing element, a glucose sensing strip, a pH sensing strip, an electrical resistance, an optical sensing element, or combinations thereof. Also, the sensed process parameter may include, but is not limited to, the pressure of the fluid in the disposable fluid coupling tubes, the temperature of the fluid, the pH of the fluid, the presence of a biomass in the fluid, the electrical conductivity of the fluid, the level of glucose in the fluid, the cell viability in the fluid, the level of oxygen in the bio-processing units, the level of carbon-dioxide in the bio-processing units, the flow rate of the fluid, the level of foam in the fluid in the bio-processing units, or combinations thereof.

The sensor further includes a wireless communication unit (410) operatively coupled to the sensing unit (408). The wireless communication unit (410) is configured to wirelessly communicate data corresponding to the sensed process parameter to the processor (202) in the power management subsystem (200). It may be noted that the sensor (400) is configured to power the sensing unit (408) and the wireless communication unit (410) using the stored energy in the energy storage unit (404). Implementing the sensor (400) as described hereinabove advantageously allows the self-powering operation of the sensor 400, while circumventing the need for any cables/connectors for powering the sensors.

Figure 5:
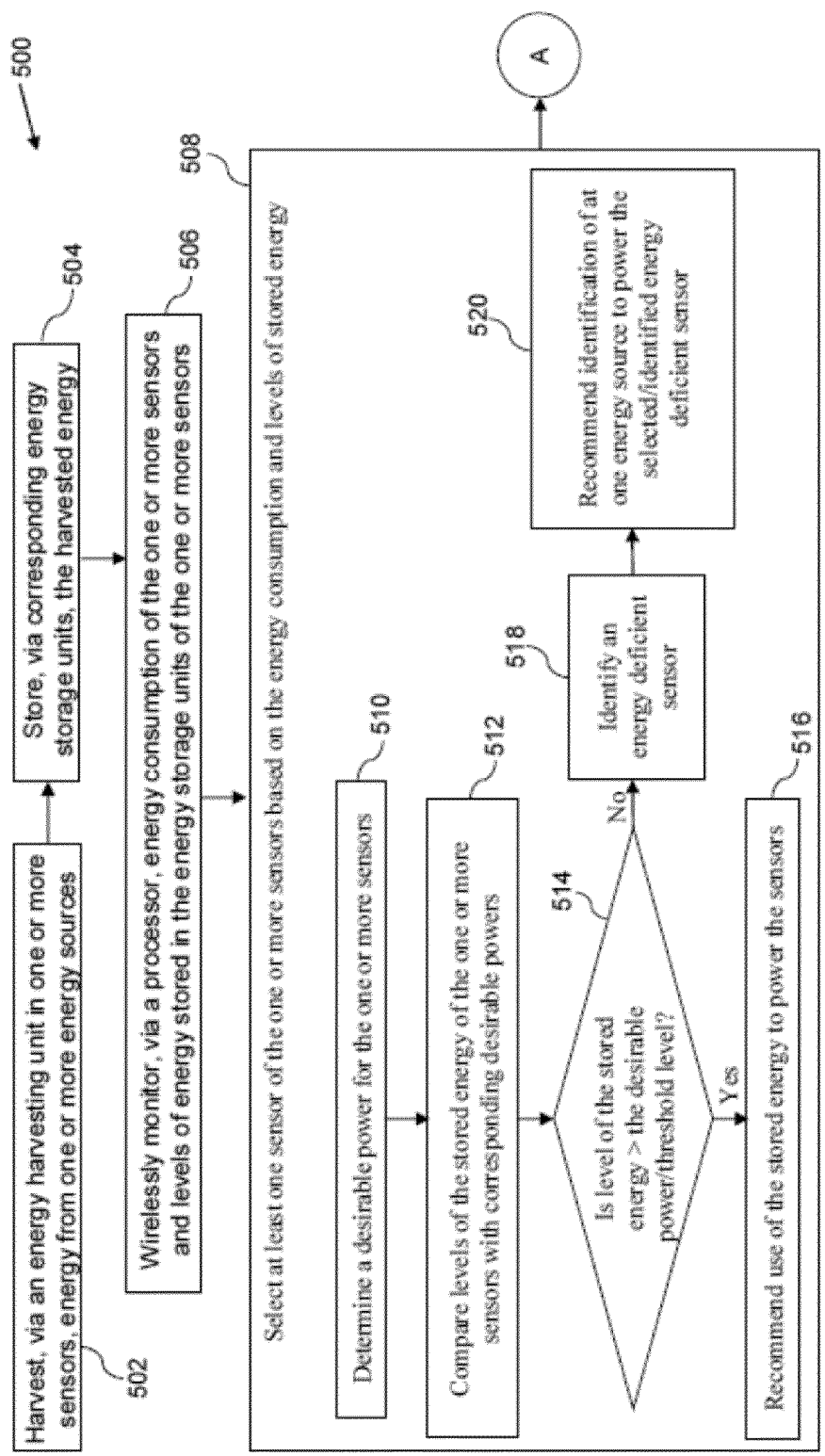
FIG. 5 is a flowchart representing a method for wirelessly powering a sensor in the bio-processing system of FIG. 1, in accordance with aspects of the present specification.

Referring now to FIG. 5, a flowchart (500) representing a method for wirelessly powering one or more sensors in a bio-processing system, such as the bio-processing system (100) of FIG. 1. The method (500) is described with reference to the components of FIGS. 1-4.

As previously noted with reference to FIG. 1, the bio-processing system (100) includes the bio-processing units (106-110), the process supporting devices (112-114), and the sensors (116-128). In addition, the bio-processing system (100) includes the power management subsystem (104) configured to manage/control supply of power to the various components of the bio-processing system (100) and the sensors (116-128), in particular.

In certain embodiments, the method (500) starts at step (502), where energy from at least one energy source of the one or more energy sources (146-150) such as the active energy sources (146-148) and the ambient energy sources (150) in the bio-processing system (100) is harvested by the energy harvesting unit (402) of the one or more sensors (400) in the bio-processing system (100). It may be noted that the energy is wirelessly harvested from the active energy sources and the surrounding ambience, thereby obviating the need for any wires and/or connectors for coupling the sensors (400) to the energy sources.

Once the energy is harvested by the energy harvesting units 402, the harvested energy is stored in the energy storage units (404) of the sensors (400), as indicated by step (504). In certain embodiments, the harvested energy may be boosted/enhanced via use of the power converter (406) prior to storage.

Subsequently, at step (506), energy consumption of the sensors (400) and levels of stored energy in corresponding energy storage units (404) is wirelessly monitored. In some embodiments, the energy consumption of the sensors (400) and levels of stored energy in corresponding energy storage units (404) are monitored by the processor (202) in the power management subsystem (200). In one example, the energy consumption may be representative of a rate of energy consumed by the sensor (400). The rate of energy consumption may be represented as mW/hour or Watts/hour.

Further, at step (508), one or more of the one or more sensors (116-128, 400) is selected/identified based on the energy consumption and levels of stored energy corresponding to the sensors (116-128, 400). More particularly, one or more energy deficient sensors may be identified/selected at step (508). The energy deficient sensor is representative of a sensor that is unable to power itself and enable a self-sustaining/self-powering sensor operation.

In accordance with aspects of the present specification, it is desirable to supply energy to the energy deficient sensor to fulfill the energy deficit in that sensor. Accordingly, a desirable power or desired power requirements corresponding to each of the one or more sensors (116-128, 400) in the bio-processing environment (102) is determined/obtained, as indicated by step (510). As previously noted, the desired power requirements corresponding to the sensors (116-128, 400) may be obtained from the catalog and/or the look-up table via use of the unique ID associated with each sensor (116-128, 400).

Additionally, in certain embodiments, at step (510), threshold levels corresponding to the desired power requirements may also be acquired from the catalog/look-up table. In alternative embodiments, the thresholds may be set and/or modified. These threshold levels are representative of an energy deficient state of the sensor (116-128, 400) at which it is desirable to switch to another energy source or harvest additional energy to power the sensor. In one example, the threshold level for a given sensor (116-128, 400) may be set at about a 50% drain off level.

Subsequently, at step (512), the levels of the stored energy of the sensors (116-128, 400) are compared to corresponding desired power requirements and/or the corresponding the threshold levels to identify one or more energy deficient sensors (116-128, 400). Accordingly, at step (514), a check is carried out to verify if the level of the stored energy of each sensor (116-128, 400) is greater than a corresponding desired power requirement and/or threshold level. Moreover, at step (514), if it is verified that the level of the stored energy of a given sensor (116-128, 400) is greater than the corresponding desired power requirement and/or threshold level, control is passed to step (516). At step (516), a recommendation indicating that the level of stored energy of that given sensor is sufficient to power that sensor (116-128, 400) is created.

However, at step (514), if it is determined that the level of the stored energy of the given sensor (116-128, 400) is lower than the corresponding desired power requirement and/or threshold level, that sensor (116-128, 400) is identified/selected as an energy deficient sensor having an inadequate level of stored energy to power the sensor, as indicated by step (518). Furthermore, since the level of the stored energy of the given sensor is inadequate to power that sensor (116-128, 400), a recommendation indicating that an additional source of the energy is needed to supply a deficit in the stored energy of the sensor (116-128, 400) is created, as depicted by step (520). Additionally, the recommendation created at step (520) may indicate a need to switch to another energy source to power the energy deficient sensor.

Figure 6:
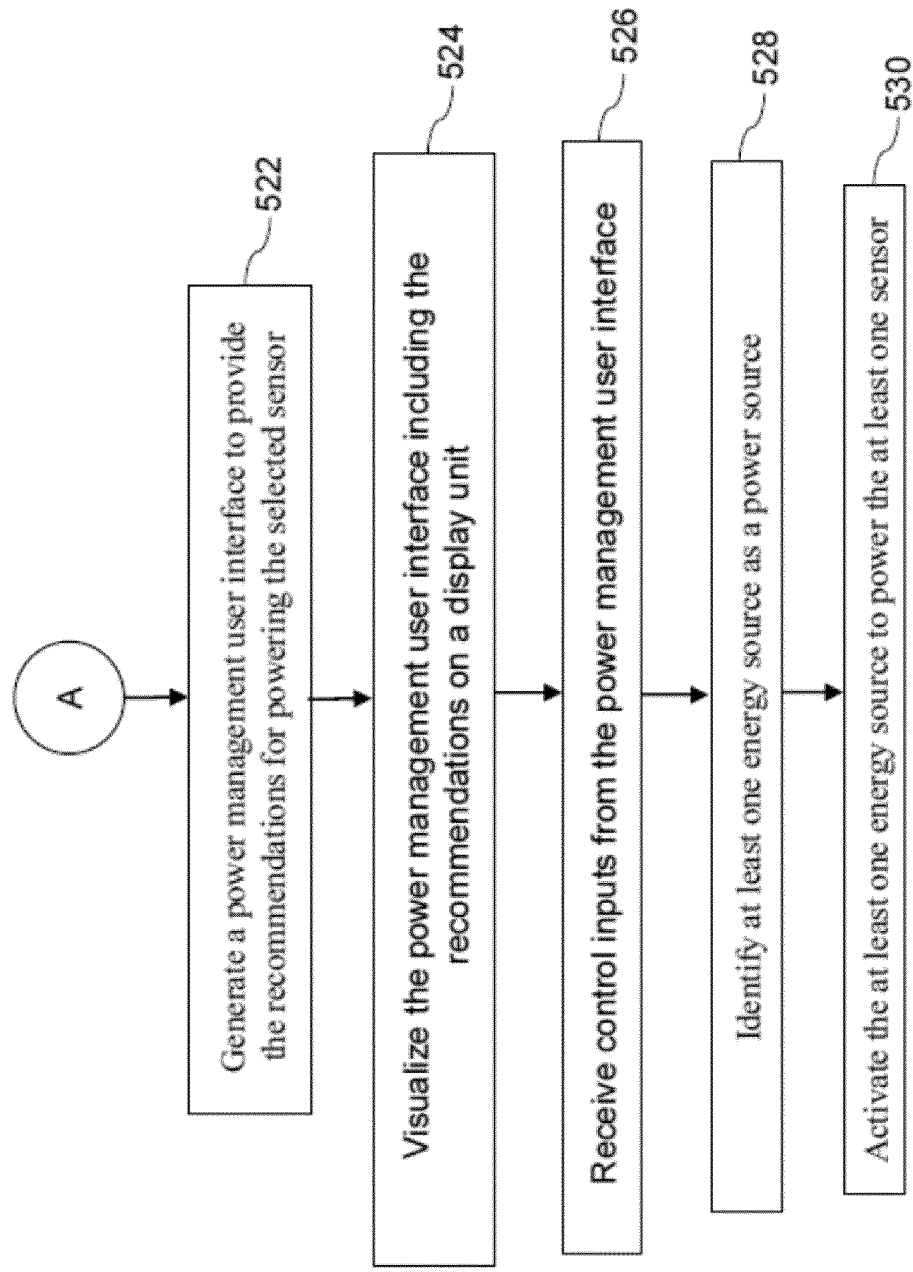
FIG. 6 is a flowchart representing an automated method for wirelessly powering the sensors.

In accordance with aspects of the present specification, the method (500) may be performed as an automated method, a semi-automated method, a manual method, or combinations thereof. In the example of an automated method for wirelessly powering the sensors (116-128, 400), control may be passed from step (520) to step (528) (FIG. 6), where at least one active energy source (146-148) is identified as a power source based on the recommendation generated at step (520). In particular, if an energy deficient sensor is identified at step 518, the processor (202) is configured to identify at least one active energy source of the active energy sources (146-148) as the power source for powering the energy deficient sensors. By way of example, an active energy source that is capable of supplying the deficit in the stored energy of the energy deficient sensor may be identified as the power source. It may be noted that information related to the energy supplying capability of each active energy source may be generated and/or retrieved from the catalog and/or look-up table. Accordingly, the processor (202) may be configured to identify at least one active energy source (146-148) based on the level of energy deficiency in the sensor and the energy supplying capability of each active energy source (146-148). In some embodiments, the processor (202) may also be configured select the active energy source (146-148) as the power source based on the locations of the energy deficient sensors and the locations of the active energy sources (146-148). Information about the locations of the sensors (116-128, 400) and the energy sources (146-150) may be stored and/or obtained from the catalog/look-up table.

Moreover, at step (530), the active energy source identified as the power source is activated to power the energy deficient sensor. In certain embodiments, the processor (202) in the power management subsystem (200) is configured activate the identified power source. More particularly, the master wireless communication unit (208) in the power management subsystem (200) is configured to aid in the wireless communication between the processor (202) and the active energy sources (146-148) to activate the identified power source to wirelessly transfer power the selected/identified energy deficient sensor (116-128, 400). In another embodiment, a smart switching device such as the smart switching devices (132-140) is configured to operatively couple the processor (202) to the active energy sources (146-148) and facilitate activation of the identified power source to wirelessly power the sensor (116-128, 400). Further, the identified power source is configured to wirelessly transfer power to the selected energy deficient sensor to supply/fulfill the energy deficit or shortfall of that sensor. By way of example, if the sensor (128) is identified as an energy deficient sensor, the processor (202) may identify the RF source (146) as a power source. The RF source (146) may be configured to wirelessly transfer power to the energy harvesting unit of the sensor (128), thereby supplying the energy deficiency of the sensor (128).

As previously noted, the method may also be performed in a manual or semi-automated mode. In this example, once the recommendation of either step (516) or step (520) is created, control is passed to step (522). At step (522), the power management user interface (300) is generated by the processor (202) based on the sensors (116-128, 400), the active energy sources (146-148), the ambient energy sources (150), the energy consumption of the given sensor (116-128, 400), the level of energy stored in the energy storage unit (404) of the given sensor (116-128, 400), desired power requirements of the sensors (116-128, 400), or combinations thereof. Additionally, the power management user interface (300) may also provide a visual representation of the recommendations created at steps (516, 520). The power management user interface (300) is visualized on the display unit (206) of the power management subsystem 200, as depicted by step (524).

Moreover, the power management user interface (300) provides a user the ability to select a type of sensor (116-128, 400). Also, the user may use the power management user interface (300) to identify an active energy source as the power source to supply the energy deficit to the selected sensor, and the like. In certain embodiments, the power management subsystem (104, 200) is configured to receive one or more selections of the user as control inputs, as indicated by step (526). Accordingly, in this example, at least one active energy source may be identified as the power source for supplying the energy deficit of the energy deficient sensor based on the received control inputs, as indicated by step (528). Subsequently, at step (530), the identified power source is activated to power the energy deficient sensor. Consequently, the energy is efficiently routed to the point of use (for example, the energy deficient sensor) while circumventing the need for cables and/or wires.

Further, one or more process parameters corresponding to the bio-processing operation being performed by the bio-processing system (100) may be sensed by the sensing units (408) of the sensors (116-128, 400). Additionally, data corresponding to the sensed process parameter(s) may be wirelessly communicated to the processor (202) from the sensor (116-128, 400). In certain embodiments, the wireless communication unit (410) of the one or more sensors (116-128, 400) may be employed to wirelessly communicate the data corresponding to the sensed process parameters to the processor (202).

The system and method for wirelessly powering one or more sensors in a bio-processing environment/system presented hereinabove provide an integrated bio-processing framework that facilitates self-powering of sensors in the bio-processing environment and wireless transfer of data in the bio-processing system. In particular, the systems and methods provide a robust framework for self-powering the sensors by wirelessly harvesting energy from active energy sources and ambient energy sources in the bio-processing environment. Use of the self-powering sensors obviates the hassle of connecting all the required sensors every time a cell bag is replaced, thereby enhancing the usability of the bio-processing system. Moreover, use of the systems and methods also allow enhanced process control as a greater number of compact sensors may be accommodated in the bio-processing system and may also be repeated at more locations. Additionally, the use of the wireless sensors enhances the clinical workflow by circumventing the need for interconnecting wires/connectors. Moreover, self-powering the sensors and wirelessly communicating data in the bio-processing environment enhances the efficiency of operation of the bio-processing system Moreover, the systems and methods for wirelessly powering the sensors enables a self-sustaining, self-powering and economical operation of the sensors in the bio-processing system. Also, various components in the bio-processing environment such as the flexible tubing and the flexible cell bags are formed using polymeric materials. Advantageously, use of these flexible, polymeric components allow use of disposable, single use components in the bio-processing environment. Also, these components may be supplied pre-sterilized, and have improved sterility, cleanability, and reduced cycle time, thereby reducing costs of running the bio-processing operation.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be limited by the foregoing description, but is only limited by the scope of the appended claims.

The invention claimed is:

1. A bio-processing system for wirelessly powering one or more sensors, the system comprising:
   one or more bio-processing units configured to perform at least one bio-processing operation;
   one or more process supporting devices operatively coupled to the one or more bio-processing units, wherein the one or more process supporting devices are configured to aid the one or more bio-processing units in performing the at least one bio-processing operation;
   one or more energy sources, wherein the one or more energy sources comprise one or more active energy sources and one or more ambient energy sources;
   one or more sensors operatively coupled to at least one of the one or more bio-processing units and the one or more process supporting devices, wherein at least one sensor of the one or more sensors comprises:
      an energy harvesting unit configured to harvest energy from at least one energy source of the one or more energy sources, and
      an energy storage unit operatively coupled to the energy harvesting unit and configured to store the harvested energy;
   a power management subsystem wirelessly coupled to the one or more sensors, wherein the power management subsystem comprises a processor configured to:
      wirelessly monitor energy consumption of the one or more sensors and a level of energy stored in corresponding energy storage units of the one or more sensors;
      select at least one energy-deficient sensor being unable to power itself and enable a self-sustaining sensor operation of the one or more sensors based on the energy consumption of the one or more sensors and corresponding levels of energy stored in the energy storage units of the one or more sensors; and
      identify at least one active energy source of the one or more active energy sources as a power source, wherein the identified power source is configured to wirelessly transfer power to the selected at least one energy-deficient sensor.

2. The bio-processing system of claim 1, wherein the one or more bio-processing units comprise one or more disposable components formed using a polymeric material.

3. The bio-processing system of claim 2, wherein the one or more sensors are disposed on one or more of the one or more disposable components of the one or more bio-processing units and disposable flexible tubing used to operatively couple the one or more bio-processing units and the one or more process supporting devices in the bio-processing system.

4. The bio-processing system of claim 1, wherein the one or more sensors comprise a pressure sensor, a temperature sensor, a pH sensor, a conductivity sensor, a glucose sensor, a biomass sensor, a cell viability sensor, an oxygen sensor, a carbon-dioxide sensor, an ultraviolet sensor, a flow sensor, a foam sensor, or combinations thereof.

5. The bio-processing system of claim 1, wherein to identify the at least one active energy source of the one or more active energy sources as the power source, the processor is further configured to:
   generate a power management user interface based on the one or more sensors, the one or more energy sources, the energy consumption of the at least one sensor, and the level of energy stored in the energy storage unit of the at least one sensor, wherein the power management user interface comprises one or more recommendations for powering the at least one sensor;
   visualize the power management user interface on a display unit of the power management subsystem;
   receive control inputs via the power management user interface; and
   activate the identified power source based on the control inputs to power the selected at least one sensor.

6. The bio-processing system of claim 5, wherein to generate the power management user interface the processor is configured to:
   obtain a desirable power for powering the at least one sensor;
   compare the level of energy stored in the energy storage unit of the at least one sensor with the desirable power corresponding to the at least one sensor; and
   create, based on the comparison, one or more recommendations for identifying the at least one active energy source as the power source for powering the at least one sensor.

7. The bio-processing system of claim 1, wherein the at least one sensor further comprises a power converter disposed between the energy harvesting unit and the energy storage unit, and wherein the power converter is configured to enhance a level of the harvested energy.

8. The bio-processing system of claim 1, wherein the at least one sensor further comprises:
   a sensing unit configured to sense a process parameter corresponding to the at least one bio-processing operation; and
   a wireless communication unit operatively coupled to the sensing unit and configured to communicate data corresponding to the sensed process parameter to the processor,
   wherein the sensing unit and the wireless communication unit are powered via the stored energy in the energy storage unit.

9. The bio-processing system of claim 1, wherein the energy harvesting unit comprises a thermo-electric generator, a Peltier element, a photovoltaic module, an electromagnetic power generation module, a piezo electric device, an inductive device, or combinations thereof, and the energy storage unit includes a rechargeable battery, a solid-state battery, a capacitor, a super-capacitor, an ultra-capacitor, or a combination thereof.

10. The bio-processing system of claim 1, wherein the power management subsystem further comprises a master wireless communication unit configured to aid in wireless communication between the processor and the one or more energy sources to activate the identified power source to power the at least one sensor.

11. The bio-processing system of claim 1, further comprising a smart switching device configured to operatively couple the processor to the one or more energy sources, wherein the smart switching device is configured to activate the identified power source.

12. The bio-processing system of claim 1, wherein the one or more active energy sources comprise a radio frequency source, a light source, a heat source, a vibration source, an ultrasound energy source, or combinations thereof.

13. The bio-processing system of claim 1, wherein the one or more ambient energy sources comprise an ambient temperature, an ambient pressure, an ambient light, an ambient radio frequency source, or combinations thereof.

14. The bio-processing system of claim 1, wherein the one or more bio-processing units comprise a bioreactor for cell cultivation, a wave rocker, a cell banking unit, a cell harvesting unit, a chromatography unit, a protein concentration unit, a sterile filtration unit, a virus removal unit, a product holding unit, a buffer preparation unit, a media preparation unit, a buffer holding unit, a media holding unit, or combinations thereof, and the one or more process supporting devices comprise a pump, a weighing scale, a flow restriction clamp, a temperature management device, or combinations thereof.

15. A method for wirelessly powering one or more sensors in a bio-processing system comprising one or more bio-processing units, one or more process supporting devices, the one or more sensors, one or more energy sources, and a power management subsystem, the method comprising:
wirelessly harvesting, via an energy harvesting unit in the one or more sensors, energy from at least one energy source of the one or more energy sources in the bio-processing system, wherein the one more energy sources comprise one or more active energy sources and one or more ambient energy sources;
storing, via an energy storage unit in the one or more sensors, the harvested energy;
wirelessly monitoring, via a processor in the power management subsystem, energy consumption of the one or more sensors and a level of energy stored in corresponding energy storage units of the one or more sensors;
selecting at least one energy-deficient sensor being unable to power itself and enable a self-sustaining sensor operation of the one or more sensors based on the energy consumption of the one or more sensors and corresponding levels of energy stored in the energy storage units of the one or more sensors; and
identifying at least one active energy source of the one or more energy sources as a power source, wherein the identified power source is configured to wirelessly power to the selected at least one energy-deficient sensor.

16. The method of claim 15, further comprising:
generating a power management user interface based on the one or more sensors, the one or more energy sources, the energy consumption of the at least one sensor, and the level of energy stored in the energy storage unit of the at least one sensor;
visualizing the power management user interface on a display unit of the power management subsystem;
receiving control inputs via the power management user interface; and
activating the identified power source based on the control inputs to power the selected at least one sensor.

17. The method of claim 15, wherein generating the power management user interface comprises:
determining a desirable power for powering the at least one sensor;
comparing the level of energy stored in the energy storage unit of the at least one sensor with the desirable power for powering the at least one sensor; and
creating, based on the comparison, one or more recommendations for identifying the at least one active energy source as the power source for powering the at least one sensor.

18. The method of claim 17, wherein creating, based on the comparison, the one or more recommendations comprises recommending one of use of the stored energy and use of the at least one active energy source to power the at least one sensor.

19. The method of claim 15, further comprising:
sensing, via a sensing unit of the one or more sensors, a process parameter corresponding to a bio-processing operation; and
wirelessly communicating, via a wireless communication unit of the one or more sensors, data corresponding to the sensed process parameter to the processor,
wherein the sensing unit and the wireless communication unit are powered via energy stored in the energy storage unit of a corresponding sensor.

20. The method of claim 15, further comprising wirelessly communicating, via a master wireless communication unit, data between the processor and the one or more energy sources to activate the identified power source to power the at least one sensor.

21. A power management subsystem for wirelessly powering one or more sensors in a bio-processing system, the bio-processing system comprising one or more bio-processing units, one or more process supporting devices operatively coupled to the one or more bio-processing units, one or more energy sources comprising one or more active energy sources and one or more ambient energy sources, the one or more sensors operatively coupled to at least one of the one or more bio-processing units and the one or more process supporting devices, wherein the power management subsystem is wirelessly coupled to the one or more sensors, the power management subsystem comprising a processor configured to:
wirelessly monitor energy consumption of the one or more sensors and a level of energy stored in corresponding energy storage units of the one or more sensors;
select at least one energy-deficient sensor being unable to power itself and enable a self-sustaining sensor operation of the one or more sensors based on the energy consumption of the one or more sensors and corresponding levels of energy stored in the energy storage units of the one or more sensors; and
identify at least one active energy source of the one or more active energy sources as a power source, wherein the identified power source is configured to wirelessly transfer power to the selected at least one energy-deficient sensor.

22. The power management subsystem of claim 21, wherein the processor is further configured to:
generate a power management user interface based on the one or more sensors, the one or more energy sources, the energy consumption of the at least one sensor, and the level of energy stored in the energy storage unit of the at least one sensor, wherein the power management user interface comprises one or more recommendations for powering the at least one sensor;
visualize the power management user interface on a display unit of the power management subsystem;
receive control inputs via the power management user interface; and
activate the identified power source based on the control inputs to power the selected at least one sensor.

23. The power management subsystem of claim 22, wherein to generate the power management user interface the processor is configured to:
- determine a desirable power for powering the at least one sensor;
- compare the level of energy stored in the energy storage unit of the at least one sensor with the desirable power corresponding to the at least one sensor; and
- create, based on the comparison, one or more recommendations for identifying the at least one energy source as the power source for powering the at least one sensor.

24. The power management subsystem of claim 21, further comprising:
- a display unit configured to visualize at least the power management user interface;
- a memory unit; and
- a master wireless communication unit configured to aid in wireless communication between the processor and the one or more energy sources to activate the identified power source to power the at least one sensor.

25. The power management subsystem of claim 21 for use in a bio-processing system.

\* \* \* \* \*